United States Patent
Denny et al.

(10) Patent No.: US 6,517,836 B1
(45) Date of Patent: Feb. 11, 2003

(54) NITROPHENYLAZIRIDINE COMPOUNDS AND THEIR USE AS PRODRUGS

(75) Inventors: William Alexander Denny, Auckland (NZ); Graham John Atwell, Auckland (NZ); Brian Desmond Palmer, Auckland (NZ); William Robert Wilson, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 0 days.

(21) Appl. No.: 09/786,588

(22) PCT Filed: Sep. 7, 1999

(86) PCT No.: PCT/GB99/02956
§ 371 (c)(1),
(2), (4) Date: Mar. 6, 2001

(87) PCT Pub. No.: WO00/13683
PCT Pub. Date: Mar. 16, 2000

(30) Foreign Application Priority Data

Sep. 7, 1998 (GB) .............................................. 9819472

(51) Int. Cl.$^7$ ...................... A61K 39/44; A61K 31/415; A61K 31/395; A61K 31/535; C07D 203/14; C07D 403/04; C07D 413/04
(52) U.S. Cl. ................................ 424/181.1; 424/178.1; 424/93.2; 514/237.2; 514/397; 514/183; 544/111; 548/314.7; 548/978
(58) Field of Search ................................ 514/340, 183, 514/237.2, 347; 424/178.1, 93.2, 181.1; 548/967, 314.7; 544/111

(56) References Cited

FOREIGN PATENT DOCUMENTS

| WO | WO 89/07592 | 8/1989 |
|---|---|---|
| WO | WO 94/21118 | 9/1994 |
| WO | WO 95/12678 | 5/1995 |
| WO | WO 97/24143 | 7/1997 |

OTHER PUBLICATIONS

Palmer et al, J. Med. Chem., 37(17),321403222 (1992).*
Anlezark et al. (1995) "Bioactivation of Dinitrobenzamide Mustards by an *E. Coli* B Nitroreductase." *Biochemical Pharmacology*, vol. 50(5):609–618.
Barton et al. (1997) "Gene therapy for ovarian carcinoma using *E. coli* nitroreductase and CB1954." *British Journal of Cancer*, vol. 76(supp. 1):40.
Bailey et al. (1996) "Investigation of alternative prodrugs for use with *E. coli* nitroreductase in 'suicide gene' approaches to cancer therapy." *Gene Therapy*, vol. 3:1143–1150.

Connors (1995) "The choice of prodrugs for gene directed enzyme prodrug therapy of cancer." *Gene Therapy*, vol. 2:702–709.
Denny et al. (1998) "The Design of Selectively–activated Anti–cancer Prodrugs for use in Antibody–directed and Gene–directed Enzyme–Prodrug Therapies." *J. Pharm.*, vol. 50:387–394.
Khan et al. (1969) "Tumour–growth inhibitory nitrophenylaziridines and related compounds: structure–activity relationships." *Chem.–Biol. Interactions*, vol. 1(1):27–47.
Khan et al. (1971) "Tumour–growth inhibitory nitrophenylaziridines and related compounds: sturcture–activity relationships. II." *Chem.–Biol. Interactions*, vol. 4(1):11–22.
Knox et al. (1988) "A New Cytotoxic, DNA Interstrand Crosslinking Agent, 5–(Aziridin–1–yl)–4–Hydroxylamino–2–nitrobenzamide, is formed from 5–)Aziridin–1–yl)–2,4–Dinitrobenzamide (CB 1954) By a Nitroreductase Enzyme in Walker Carcinoma Cells." *Biochemical Pharmacology*, vol. 37(24):4661–4669.
Knox et al. (1991) "Bioactivation of CB 1954: Reaction of the Active 4–Hydroxylamino derivative with Thioesters to Form the Ultimate DNA—DNA Interstrand Crosslinking Species." *Biochemical Pharmacology*, vol. 42(9):1691–1697.
Lewis (1989) "Molecular orbital calculations on tumour–inhibitory phenyl aziridines: QSARs." *Xenobiotica*, vol. 19(3):341–356.
McNeish et al. (1998) "Virus directed enzyme prodrug therapy for ovarian and pancreatic cancer using retrovirally delivered *E. coli* nitroreductase and CB1954." *Gene Therapy*, vol. 5:1061–1069.
McNeish et al. (1997) "Gene directed enzyme prodrug therapy for cancer." *Advanced Drug Delivery Reviews*, vol. 26:173–184.
Niculescu–Duvaz et al. (1997) "Antibody–directed enzyme prodrug therapy (ADEPT): a review." *Advanced Drug Delivery Reviews*, vol. 26:151–172.

* cited by examiner

*Primary Examiner*—Mary E. Ceperley
(74) *Attorney, Agent, or Firm*—Pamela J. Sherwood; Bozicevic, Field & Francis LLP

(57) ABSTRACT

A range of aziridin-1-yl nitrobenzamides are provided for use as prodrugs in conjunction with nitroreductase (NR) enzymes. The amides may have 1 or 2-substituents which may be bulky and polar. For example, 5-(aziridin-1-yl)-N-[2-(4-morpholino)ethyl]-2,4-dinitrobenzamide of Formula (A) was found to be highly active against all NR+ cell lines tested.

8 Claims, No Drawings

NITROPHENYLAZIRIDINE COMPOUNDS AND THEIR USE AS PRODRUGS

The present invention relates to novel nitrophenylaziridines, and is particularly concerned with the use of these compounds as anti-cancer agents, as well as prodrugs for antibody-directed enzyme-prodrug therapy (ADEPT) and gene-directed enzyme-prodrug therapy (GDEPT), in conjunction with nitroreductase enzymes.

BACKGROUND OF THE INVENTION

The use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an is enzyme monoclonal/antibody conjugate represents a very powerful clinical agent. This approach to cancer therapy, often referred to as "antibody directed enzyme/prodrug therapy" (ADEPT) is disclosed in WO88/07378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al., Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, Annu. Rev. Biochem., 1993, 62;191. The term "GDEPT" (gene-directed enzyme prodrug therapy) is used to include both viral and non-viral delivery systems.

A number of nitrophenylaziridines have been reported as antitumour agents (Cobb et al., Biochem. Pharmacol., 1969, 18, 1519–1527; Khan and Ross, Chem.-Biol. Int., 1971, 4, 11–22; Workman et al., Cancer Chemother. Pharmacol., 1986, 16, 9–14; Roberts et al., WO 89/07592). One example [CB 1954: 5-(aziridin-1-yl)-2,4-dinitrobenzamide] has also been reported to be a substrate for both DT diaphorase (Knox et al., Biochem. Pharmacol., 1988, 37, 4661–4669 and 4671–4677) and the aerobic nitroreductase (NR) isolated from $E.\ coli$ B (Boland et al., Biochem. Pharmacol. 1991, 41, 867–875; Anlezark et al., Biochem. Pharmacol, 1992, 44, 2289–2295). This compound has also been used as a prodrug in both ADEPT (Knox et al., Biochem. Pharmacol., 1995, 49, 1641–1647) and GDEPT (Bridgewater et al., Eur. J. Cancer, 1995, 31A, 2362–2370; Bailey et al., Gene Ther., 1996, 3, 1143–1150; Bailey and Hart, Gene Ther., 1997, 4, 80–81; Green et al., Cancer Gene Ther., 1997, 4, 229–238) applications.

DISCLOSURE OF THE INVENTION

In a first aspect, the present invention relates to the use of a class compounds represented by the general formula (I) for the manufacture of a medicament for treatment of neoplastic disease in combination with a nitroreductase enzyme:

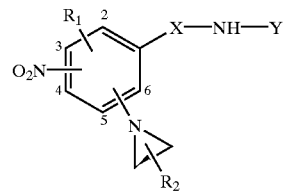

wherein:

X represents CO or $SO_2$;

Y represents H, or a lower alkyl group being optionally substituted with one or more of the following groups: hydroxy, alkoxy, halo, N-oxy, amino, alkylamino, dialkylamino, imidazolyl, alkylpiperazinyl and morpholino, thio and thioether; and $R_1$ represents at any available aromatic ring position, H, halo, $NO_2$, $N_3$, CN, $SOCH_2Y$, $SO_2CH_2Y$, $COCH_2Y$, SONHY, $SO_2NHY$, CONHY, $CO_2Y$ or a lower alkyl group being optionally substituted with one or more of the following groups: hydroxy, alkoxy, halo, N-oxy, amino, alkylamino, dialkylamino, imidazolyl, alkylpiperazinyl, morpholino, thio and thioether;

or $R_1$ may represent the replacement of one —CH= group in the aromatic ring by an —N= (aza) group;

the aziridine may be at any available aromatic ring position;

$R_2$ represents the optional presence at either or both aziridine ring positions independently one or more substituents independently selected from methyl or ethyl;

provided that when X is CO, $R_1$ is an $NO_2$ group, the two $NO_2$ groups being in the 2 and 4 positions on the ring, and the aziridine is in the 5 position, and there are no substituents on the aziridine ring, then Y is not H.

The nitroreductase enzyme is generally present in the patient to be treated, preferably at the site of the tumour. Delivery of the enzyme to the tumour may be achieved by linking it to a monoclonal antibody which will bind to a tumour associated antigen, or by targeting the tumour cells with a viral vector carrying a gene encoding of the enzyme.

A second aspect of the present invention relates to compounds of formula (I):

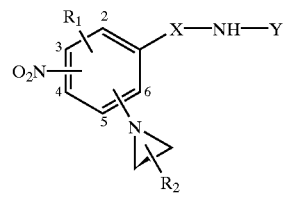

wherein:

X represents CO or $SO_2$;

Y represents H, or a lower alkyl group being optionally substituted with one or more of the following groups: hydroxy, alkoxy, halo, N-oxy, amino, alkylamino, dialkylamino, imidazolyl, alkylpiperazinyl and morpholino, thio and thioether; and $R_1$ represents at any available aromatic ring position, H, halo, $NO_2$, $N_3$, CN, $SOCH_2Y$, $SO_2CH_2Y$, $COCH_2Y$, SONHY, $SO_2NHY$, CONHY, $CO_2Y$ or a lower alkyl group being optionally substituted with one or more of the following groups: hydroxy, alkoxy, halo, N-oxy, amino, alkylamino, dialkylamino, imidazolyl, alkylpiperazinyl, morpholino, thio and thioether;

or $R_1$ may represent the replacement of one —CH= group in the aromatic ring by an —N= (aza) group;

the aziridine may be at any available aromatic ring position;

$R_2$ represents the optional presence at either or both aziridine ring positions independently one or more substituents independently selected from methyl or ethyl;

provided that when X is CO, $R_1$ is an $NO_2$ group, the two $NO_2$ groups being in the 2 and 4 positions on the ring, if the aziridine is in the 5 position and there are no substituents on the aziridine ring, then Y is not H, or an unsubstituted lower alkyl having 1 to 6 carbon atoms;

and provided that when X is CO, $R_1$ is an $NO_2$ group, the two $NO_2$ groups being at the 3 and 5 positions, if the aziridine is in the 2 position and there are no substituents on the aziridine ring, then Y is not H;

and provided that when X is CO, $R_1$ is an $NO_2$ group, the two $NO_2$ groups being at the 3 and 5 positions, if the aziridine is in the 4 position and there are no substituents on the aziridine ring, then Y is not H;

and provided that when X is $SO_2$, $R_1$ is H, the $NO_2$ group is in the 3 position, if the aziridine is in the 4 position, and there are no substituents on the aziridine ring, then Y is not H;

and provided that when X is CO and Y is H, $R_1$ is an $NO_2$ group, the two $NO_2$ groups being in the 2 and 4 positions, if the aziridine is in the 5 position, then $R_2$ is not a methyl, two methyls or an ethyl group at a single position of the aziridine ring.

In this application, 'lower alkyl' represents a straight or branched alkyl group having 1 to 6 carbon atoms, for example, methyl, ethyl, propyl, cyclopentyl, and more preferably methyl or ethyl. 'Halo' represents a radical of any of the halogens, e.g. F, Cl, I, Br. The 'alkyl' in alkylamino, dialkylamino and alkyl piperazinyl represents an alkyl group of 1 to 10 carbon atoms, more preferably 1 to 6 carbon atoms, and most preferably methyl or ethyl. 'Thioether' represents a sulphur atom attached to an alkyl group, wherein the alkyl group has 1 to 10 carbon atoms, and more preferably 1 to 6 carbon atoms. 'Alkoxy' represents an oxygen atom attached to an alkyl group, wherein the alkyl group has 1 to 10 carbon atoms, and more preferably 1 to 6 carbon atoms. 'Substituted with one or more' means substitution with, for example one, two, three, four, but more preferably only one or two, groups.

The invention also comprises salts forms of the basic or acidic compounds of formula (I) as defined in the second aspect that form pharmaceutically acceptable salts with both organic and inorganic acids and/or organic and inorganic bases. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, and the like. Examples of suitable bases for salt formation are sodium and potassium carbonate, sodium and potassium hydroxide, ammonia, triethylamine, triethanolamine, and the like.

In preferred embodiments of either the first or second aspects of the present invention, X is CO. It is further preferred that there are no substituents on the aziridine ring, and more preferred that $R_1$ is either $NO_2$ or halo. These preferences may be in combination with each other, or separately.

In either the first or second aspects of the present invention, it is preferred that the compound is of the general formula (Ia):

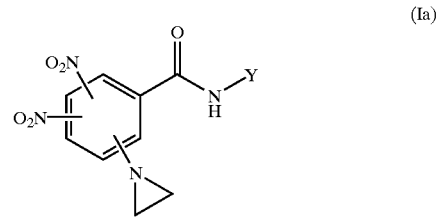

(Ia)

where Y is as defined for formula (I) in either the first or second aspect, with the exceptions as listed. It is further preferred in one alternative, that the aziridin-1-yl is in the 5 position on the aromatic ring, that the two $NO_2$ groups are in the 2 and 4 position on the aromatic ring, and that Y is a lower alkyl group having 1 to 6 carbon atoms and being substituted with one or more of the following groups: hydroxy, alkoxy, amino, halo, N-oxy, dialkylamino, imidazolyl, methylpiperazinyl, morpholinyl, thio and thioether. It is further preferred in a second alternative that Y is H.

In a different preferred embodiment of the first and second aspects of the present invention, the compound is of the general formula (Ib):

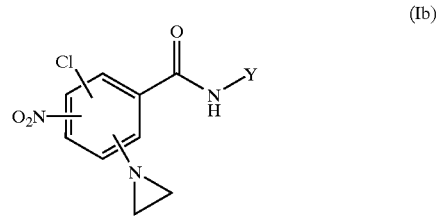

(Ib)

where Y is as defined for formula (I) in either the first or second aspect, with the exceptions as listed. It is further preferred that Y is H.

A further aspect of the invention is a method of preparing compounds of the general formula (I), from compounds of general formula (IV):

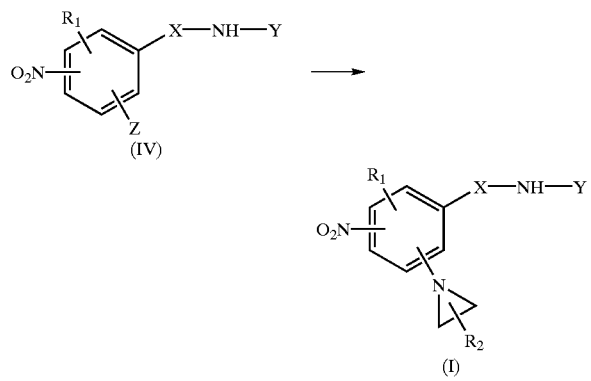

wherein X, Y, $R_1$ and $R_2$ are as designated for formula (I) in the first aspect of the invention, with the exceptions listed, and Z is F, Cl, Br or I. The amides (IV) are then reacted with aziridine (optionally substituted with $R_2$) to provide the desired compounds of formula (I). Compounds of formula (IV) may be prepared from acid chlorides of formula (III):

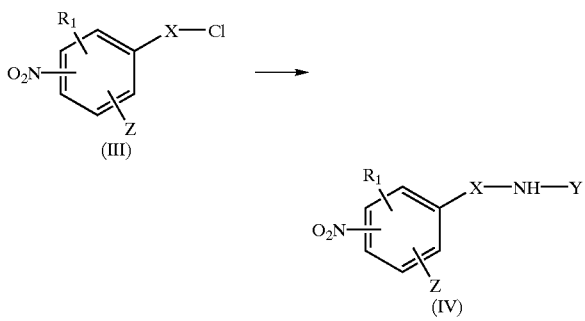

wherein X, Z and $R_1$ are as designated for formula (I) in the first aspect of the invention, with the exceptions listed, by reacting them with amines $H_2NY$, where Y is as designated for formula (I) in the first aspect of the invention.

Compounds of formula (III) may be prepared from acids of formula (II):

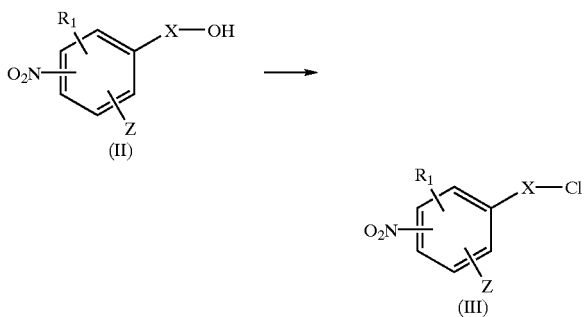

wherein X, Z and $R_1$ are as designated for formula (I) in the first aspect of the invention, with the exceptions listed, by reacting them with thionyl chloride.

Compounds of formula (II) are readily prepared by literature methods, such as described in Palmer, et al., J. Med. Chem., 1996, 39, 2518.

Another aspect of the invention relates to the use of the compounds of formula (I) as defined in the second aspect of the invention as anti-tumour agents.

In a further preferred aspect, the present invention relates to the use of the compounds of formula (I) as defined in the first aspect of the invention, with the exceptions listed, in conjunction with nitroreductase enzyme (for example, isolated from E. coli) in methods of ADEPT and GDEPT therapy. The drug produced by the action of the nitroreductase enzyme on the compounds of formula (I) may be used for the selective killing of oxic and hypoxic tumour cells in methods of treatment of cancers, for example leukemias and particularly solid cancers including breast, bowel and lung tumours, including small cell lung carcinoma.

The invention also provides pharmaceutical compositions comprising a compound of the formula (I) as defined in the first aspect, with the exceptions listed, of the invention together with a pharmaceutically acceptable carrier or diluent.

DETAILED DESCRIPTION OF THE INVENTION

GDEPT
Vector Systems

In general, the vector for use in GDEPT therapies may be any suitable DNA or RNA vector.

Suitable viral vectors include those which are based upon a retrovirus. Such vectors are widely available in the art.

Huber et al. (ibid) report the use of amphotropic retroviruses for the transformation of hepatoma, breast, colon or skin cells. Culver et al. (Science (1992) 256; 1550–1552) also describe the use of retroviral vectors in GDEPT. Such vectors or vectors derived from them may also be used. Other retroviruses may also be used to make vectors suitable for use in the present invention. Such retroviruses include rous sarcoma virus (RSV).

Englehardt et al. (Nature Genetics (1993) 4; 27–34) describe the use of adenovirus based vectors in the delivery of the cystic fibrosis transmembrane conductance product (CFTR) into cells, and such adenovirus based vectors may also be used. Vectors utilising adenovirus promoter and other control sequences may be of use in delivering a system according to the invention to cells in the lung, and hence useful in treating lung tumours.

Other vector systems including vectors based on the Molony murine leukaemia virus are known (Ram, Z et al. Cancer Research (1993) 53; 83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation ATG is supplied to direct efficient translation of the enzyme.

Suitable promoters which may be used in vectors described above, include MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

Nitroreductase

Compounds of the formula (I) can be activated by reduction of one (or more) of the available nitro groups by nitroreductase.

Preferably, the enzyme is a non-mammalian nitroreductase enzyme, such as a bacterial nitroreductase. An E.coli nitroreductase as disclosed in WO93/08288 is particularly preferred. The enzyme may be modified by standard recombinant DNA techniques, e.g. by cloning the enzyme, determining its gene sequence and altering the gene sequence by methods such as truncation, substitution, deletion or insertion of sequence s for example by site-directed mutagenesis. Reference may be made "Molecular Cloning" by Sambrook et al. (1989, Cold Spring Harbor) for discussion of standard recombinant DNA techniques. The modification made may be any which still leaves the enzyme with the ability to reduce the nitro group in formula I or II but alters other properties of the enzyme, for example its rate of reaction or selectivity.

In addition, small truncations in the N- and/or C-terminal sequence may occur as a result of the manipulations required to produce a vector in which a nucleic acid sequence encoding the enzyme is linked to the various other vector sequences.

ADEPT

For applications in ADEPT systems, an antibody directed against a tumour specific marker is linked to the nitroreductase enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, e.g. as described in EP-A-239400.

The antibodies may be produced by conventional hybridoma techniques or, in the case of modified antibodies or fragments, by recombinant DNA technology, eg by the expression in a suitable host vector of a DNA construct encoding the modified antibody or fragment operably linked to a promoter. Suitable host cells include bacterial (eg. *E.coli*), yeast, insect and mammalian. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

Applications of the Invention

Compounds of the invention can be used in vitro or in vivo for a range of applications. For example, a number of vector systems for the expression of nitroreductase in a cell have been developed. The further development of such systems (e.g. the development of promoters suitable for specific cell types) requires suitable candidate prodrugs capable of killing cells when activated by nitroreductase. Prodrug compounds of the present invention may be used in such model systems. The model systems may be in vitro model systems or xenograft model systems comprising for example human tumour cells implanted in nude mice.

Compounds of the invention which are not activatable by an enzyme may be tested in vitro against panels of different tumour cells types to determine efficacy against such tumour cells. The efficacy of compounds of the invention against a range of tumour cell types may be used as points of reference for the development of further antitumour compounds. Compounds of the present invention may also be tested in combination with additional anti-cancer compounds to determine potential combination drug systems, for example combinations which are synergistic.

The compounds of the invention may also be used in a method of treatment of the human or animal body. Such treatment includes a method of treating the growth of neoplastic cells in a patient with neoplastic disease which comprises administering to a patient in need of treatment compounds of formula (I) of the invention as part of an ADEPT or GDEPT therapy system. Neoplastic diseases include leukaemia and solid tumours such as breast, bowel and lung tumours including small cell lung carcinoma.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

ADEPT Therapy

The antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour, and the premature release of the compound produced by the action of the nitroreductase on the compound of formula (I) is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably about from 10 to 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable cofactor for the enzyme. Suitable cofactors include a riboside or ribotide of nicotinic acid or nicotinamide.

The antibody/enzyme conjugate may be administered by any suitable route usually used in ADEPT therapy. This includes parenteral administration of the antibody in a manner and in formulations similar to that described below.

GDEPT Therapy

For use of the vectors in therapy, the vectors will usually be packaged into viral particles and the particles delivered to the site of the tumour, as described in for example Ram et al. (ibid). The viral particles may be modified to include an antibody, fragment thereof (including a single chain) or tumour-directed ligand to enhance targeting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. Viruses, for example isolated from packaging cell lines may also be administered by regional perfusion or direct intratumoral direction, or direct injection into a body cavity (intracaviterial administration), for example by intra-peritoneum injection.

The exact dosage regime for GDEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of modified virus and administration by the intravenous route is frequently found to be the most practical.

In GDEPT systems the amount of virus or other vector delivered will be such as to provide a similar cellular concentration of enzyme as in the ADEPT system mentioned above. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably about from 10 to 100 mg/Kg per patient per day.

Administration of Prodrug

While it is possible for the compounds of formula (I) to be administered alone it is preferable to present them as pharmaceutical formulations. The formulations comprise the compounds, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes includes for example, those comprising the positively charged lipid (N[1-(2,3-dioleyloxy)propyl]-N,N,N-triethylammonium (DOTMA), those comprising dioleoylphosphatidylethanolamine (DOPE), and those comprising 3β[N-(N',N'-dimethylaminoethane)-carbamoyl]cholesterol (DC-Chol).

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of a patient. Preferred routes of administration are oral delivery and injection, typically parenteral or intramuscular injection or intratumoral injection.

The exact dosage regime will, of course, need to be determined by individual clinicians for individual patients and this, in turn, will be controlled by the exact nature of compound of formula (I) but some general guidance can be given. Typical dosage ranges generally will be those described above which may be administered in single or multiple doses. Other doses may be used according to the condition of the patient and other factors at the discretion of the physician. The invention will now be illustrated with reference to components 1–19 as set out below in Table 1. Compound 1 is the known compound CB1954 whereas compounds 2–19 are compounds embodying the invention and/or whose uses embody the invention.

PREPARATIVE EXAMPLES

TABLE 1

| No | Fm | $R^1$ | $R^{11}$ | $R^{111}$ | X | Y |
|----|----|----|----|----|----|----|
| 1  | A  | $NO_2$ | $NO_2$ | H | H | H |
| 2  | A  | $NO_2$ | $NO_2$ | H | H | dhp |
| 3  | A  | $NO_2$ | $NO_2$ | H | H | mph-Et |
| 4  | A  | $NO_2$ | $NO_2$ | H | Me | mph-Et |
| 5  | A  | $NO_2$ | $NO_2$ | H | H | mph-Pr |
| 6  | A  | $NO_2$ | $NO_2$ | H | H | mph-Bu |
| 7  | A  | $NO_2$ | $NO_2$ | H | H | im-Et |
| 8  | A  | $NO_2$ | $NO_2$ | H | H | $(CH_2)CO_2Me$ |
| 9  | A  | H | $NO_2$ | H | H | H |
| 10 | A  | $SO_2Me$ | $NO_2$ | H | H | dhp |
| 11 | A  | $NO_2$ | H | H | H | H |
| 12 | A  | $NO_2$ | $SO_2Me$ | H | H | H |
| 13 | A  | $NO_2$ | H | $NO_2$ | H | H |
| 14 | B  | $NO_2$ | H | $NO_2$ | H | H |
| 15 | B  | $NO_2$ | Cl | $NO_2$ | H | H |
| 16 | B  | H | Cl | $NO_2$ | H | H |
| 17 | B  | $NO_2$ | H | $NO_2$ | H | dhp |
| 18 | B  | $NO_2$ | H | $NO_2$ | H | mph-Et |
| 19 | C  | $NO_2$ | $NO_2$ | — | H | H |

Abbreviations
Fm = formula
dhp = 2,3-dihydroxypropyl(—$CH_2$.CHOH.$CH_2$OH)
mph-Et = 2-(4-morpholino)ethyl
mph-Pr = 3-(4 morpholino)propyl
mph-Bu = 4-(4 morpholino)butyl
im-Et = 2-(imidazol)ethyl Example A Preparation of N-(2,3-dihydroxypropyl)-5-(aziridin-1-yl)-2,4-dinitrobenzamide (2). A solution of N-(2,3- dihydroxypropyl)-5-chloro-2,4-dinitrobenzamide (Friedlos et al., J. Med. Chem., 1997, 40, 1270–1275) (0.50 g, 1.56 mmol) and aziridine (1.00 g, 0.023 mol) in EtOAc (100 mL) was stirred at room temperature for 18 h. After washing with water the solution was worked up to give 2 (0.43 g, 84%): mp (EtOAc/petroleum ether) 145–147° C., $^1$H NMR [(CD$_3$)$_2$SO] δ8.74 (t, J=5.7 Hz, 1H, NH), 8.64 (s, 1H, H-3), 7.43 (s, 1H, H-6), 4.85 (d, J=4 9 Hz, 1H, OH), 4.58 (t, J=5 7 Hz, 1H, OH), 3 62 (m, 1H, CHOH), 3.44–3.36 (m, 2H, CH$_2$OH), 3.39–3.36 (m, 1H, CONHCHH), 3.16–3.09 (m, 1H, CONHC), 2 48 (s, 4H, aziridine-H); $^{13}$C NMR δ164.19 (s), 152.98 (s), 139.70 (s), 138.89 (s), 137 53 (s), 124 57 (d), 122.58 (d), 70.02 (d), 63.70 (t), 42.73 (t), 29.91 (t). Anal. Calcd. for C$_{12}$H$_{14}$N$_4$O$_7$. C, 44.18;H, 4.33; N, 17.17%. Found: C, 44.22; H, 4.25; N, 17 40%.

Example B

Preparation of 5-(aziridin-1-yl)-N-[2-(4-morpholino) ethyl]-2,4-dinitrobenzamide (3). A mixture of 5-chloro-2,4-dinitrobenzoic acid (2.00 g, 8.11 mmol) and SOCl$_2$ (50 mL) containing DMF (1 drop) was refluxed under nitrogen for 18 h before concentration to dryness. The resulting crude 5-chloro-2,4-dinitrobenzoyl chloride was dissolved in dry Et$_2$O (100 mL) and the solution cooled to 0° C. and treated in one portion with a solution of 4-(2-aminoethyl) morpholine (1 96 g, 15 mmol) in Et$_2$O (20 mL). After stirring at this temperature for 15 min the resultant solid was filtered off, dissolved in water (50 mL), and treated with an excess of saturated aqueous NaHCO$_3$. The mixture was extracted with EtOAc and the extract worked up to give 5-chloro-N-[2-(4-morpholino)ethyl]-2,4-dinitrobenzamide (1.44 g, 49%): mp (EtOAc/petroleum ether) 124° C. (dec.); $^1$H NMR [(CD$_3$)$_2$SO] δ8.83 (t, J=5.4 Hz, 1H, NH), 8.83 (s, 1H, H-3), 8.10 (s, 1H, H-6), 3.58 (t, J=4.55 Hz, 4H, CH$_2$O), 3.39–3.30 (m, 2H, CONHCH$_2$), 2.47 (t, J=6.7 Hz, 2H, CH$_2$Nmorph), 2.41 (br s, 4H, NCH$_2$); $^{13}$C NMR 162.58 (s), 147 09 (s), 144 99 (s), 136 18 (s), 132.33 (d), 130.33 (s), 122.11 (d), 66.09 (t), 56.61 (t), 53.13 (t), 36.40 (t). Anal. Calcd. for C$_{13}$H$_{15}$ClN$_4$O$_6$. C, 43.53;H, 4.21; N, 15,62. Found: C, 43.90; H, 4.18; N, 15.52%.

A solution of the above amide (0.50 g, 1.39 mmol) and aziridine (1.00 g, 29 mmol) in EtOAc (80 mL) was stirred at room temperature for 18 h After washing with water the solution was dried over Na$_2$SO$_4$ and concentrated under reduced pressure to ca. 20 mL. Petroleum ether was added until a slight cloudiness persisted and the solution was chilled at −20° C. to give 3 as coarse yellow needles (0 37 g, 73%): mp 159° C., $^1$H NMR [(CD$_3$)$_2$SO] δ8.70 (t, J=5.6 Hz, 1H, NH), 8.66 (s, 1H, H-3), 7.40 (s, 1H, H-6), 3.57 (t, J=4 6 Hz, 4H, CH$_2$O), 3.40–3.29 (m, 4H, NH(CH$_2$)$_2$), 2 48 (s, 4H, aziridine-H), 2.41 (br t, J=4 6 Hz, 4H, CH$_2$N); $^{13}$C NMR δ163.97 (s), 153.03 (s), 139.72 (s), 138 82 (s), 137.49 (s), 124 42 (d), 122 68 (d), 66.12 (t), 56.68 (t), 53.17 (t), 36.40 (t), 29.90 (t). Anal. Calcd. for C$_{15}$H$_{19}$N$_5$O$_6$; C, 49 31;H, 5 25, N, 19.17 Found: C, 49.49;H, 5.26; N, 19.12%

Example C

Preparation of 5-(aziridin-1-yl)-N-methyl-N-[2-(4-morpholino)ethyl]-2,4-dinitrobenzamide (4). Similar reaction of crude 5-chloro-2,4-dinitrobenzoyl chloride in Et$_2$O with 4-[2-(methylamino)ethyl]morpholine (2 equiv) in water, followed by chromatography of the product on alumina-90, eluting with EtOAc, gave 5-chloro-N-methyl-N-[2-(4-morpholino)ethyl]-2,4-dinitrobenzamide (48%), mp (EtOAc/iPr$_2$O) 123–123.5° C. $^1$H NMR [(CD$_3$)$_2$SO] [rotamer mixture] δ8.94 & 8.94 (2xs, 1H, H-3), 8.13 & 8.09 (2xs, 1H, H-6), [3.63–3.54 (m), 3.51, t (J=4.6 Hz) & 3.28–3.18(m), 6H, O(CH$_2$)CH$_2$, N(CH$_3$)CH$_2$], 3.05 & 2.89 (2xs, 3H, CH$_3$), [2.57 (t, J=6.6 Hz), 2.50–2.38 (m) & 2.25 (t, J=4 3 Hz), 6H, CH$_2$N(CH$_2$)CH$_2$]. Anal. Calcd. for C$_{14}$H$_{17}$ClN$_4$O$_6$: C, 45.11,H, 4.60; N, 15.03. Found: C, 45.01;H, 4,43, N, 15.02%.

A stirred solution of the above benzamide (200 mg, 0.54 mmol) in CH$_2$Cl$_2$ (15 mL) was treated with aziridine (112 μL, 2.16 mmol) at room temperature for 3 h After washing with water (2x), ther solution was dried and evaporated under reduced pressure. The residue was dissolved in EtOAc, filtered through a column of alumina-90, then diluted with petroleum ether to precipitate 4 (147 mg, 72%) as an unstable gum. $^1$H NMR [(CD$_3$)$_2$SO] [rotamer mixture] δ8.77 & 8.77 (2xs, 1H, H-3), 7.44 & 7 36 (2xs, 1H, H-6), [3.64–3.53 (m), 3.49 (t, J=4 5 Hz) & 3.26–3.15 (m), 6H, O(CH$_2$)CH$_2$, N(CH$_3$)CH$_2$], 3.05 & 2.85 (2xs, 3H, CH$_3$), [2.58 (t, J=6.3 Hz), 2.53–2.39 (m) & 2.24 (t, J=4.2 Hz), 10H, CH$_2$N(CH$_2$)CH$_2$, aziridine-H]. Anal. Calcd for C$_{16}$H$_{21}$N$_5$O$_6$. C, 50 66, H, 5.58. Found C, 51.04;H, 5 80%.

Example D

Preparation of 5-(aziridin-1-yl)-N-[3-(4-morpholino) propyl]-2,4-dinitrobenzamide (5). Similar reaction of crude 5-chloro-2,4-dinitrobenzoyl chloride in Et$_2$O with 4-(3-aminopropyl)morpholine (2 equiv) in water gave 5-chloro-N-[3-(4-morpholino)propyl]-2,4-dinitrobenzamide (81%) mp (CH$_2$Cl$_2$/petroleum ether) 167–168° C.; 1H NMR [(CD$_3$)$_2$SO] δ8.85 (t, J=5 5 Hz, 1H, NH), 8.83 (s, 1H, H-3), 8 13 (s, 1H, H-6), 3.57 (t, J=4.6 Hz, 4H, CH$_2$(CH$_2$)O), 3.32–3.23 (m, 2H, NHCH$_2$), 2.24–2.29 (m, 6H, CH$_2$N(CH$_2$) CH$_2$), 1.67 (pent, J=7.0 Hz, 2H, CH$_2$CH$_2$CH$_2$). Anal. Calcd for C$_{14}$H$_{17}$ClN$_4$O$_6$: C, 45.11;H, 4.60; N, 15.03. Found: C, 45.22,H, 4.46; N, 14.94%.

Reaction of the above benzamide (200 mg, 0.54 mmol) in CH$_2$Cl$_2$ (10 mL) with aziridine (112 μL, 2.16 mmol) for 3 h at 20° C., followed by partition between more CH$_2$Cl$_2$ and water, gave 5 (114 mg, 56%): mp (CH$_2$Cl$_2$/EtOAc/petroleum ether) 151–152° C.; $^1$H NMR [(CD$_3$)$_2$SO] δ8.71 (t, J=5.4 Hz, 1H, NH), 8.65 (s, 1H, H-3), 7.41 (s, 1H , H-6), 3.57 (t, J=4.5 Hz, 4H, CH$_2$(CH$_2$)O), 3.30–3.23 (m, 2H, NHCH$_2$), 2.48 (s, 4H, aziridine-H), 2.41–2.30 (m, 6H, CH$_2$N(CH$_2$)CH$_2$), 1.68 (pent, J=7 0 Hz, 2H, CH$_2$CH$_2$CH$_2$). Anal. Calcd for C$_{16}$H$_{21}$N$_5$O$_6$: C, 50.65;H, 5.58; N, 18.46. Found; C, 50 61,H, 5.75; N, 18.33%.

Example E

Preparation of N-[4-(4-morpholino)butyl]-5-(aziridin-1-yl)-2,4-dinitrobenzamide (6). Similar reaction of crude 5-chloro-2,4-dinitrobenzoyl chloride in Et$_2$O with 4-(4-aminobutyl)morpholine (2 equiv) in water, followed by chromatography of the product on alumina-90 and elution with CH$_2$Cl$_2$/EtOAc (1.3) gave 5-chloroN-[4-(4-morpholino)butyl]2,4-dinitrobenzamide (58%): mp (EtOAc/iPr$_2$O) 116–117° C., $^1$H NMR [(CD$_3$)$_2$SO] δ8 84 (t, J=5.5 Hz, 1H, NH), 8 83 (s, 1H, H-3), 3.56 (t, J=4 5 Hz, 4H, CH$_2$(CH$_2$)O), 3.25 (q, J=6.0 Hz, 2H, NHCH$_2$), 2.33 (br s, 4H, N(CH$_2$)CH$_2$), 2.28 (t, J=6.6 Hz, 2H, CH$_2$Nmorph), 1 44 (m 4H, CH$_2$(CH$_2$)$_2$) Anal. Calcd for C$_{15}$H$_{19}$ClN$_4$O$_6$. 46.58, H, 4.95; N, 14.49. Found: C, 46.69;H, 5.19, N, 14.33%

Reaction of the above benzamide with aziridine in CH$_2$Cl$_2$ as above, followed by chromatography of the product on alumina-90 and elution with EtOAc, gave unstable 6 (62%): mp (EtOAc/petroleum ether) 118–122° C.;, $^1$NMR [(CD$_3$)$_2$SO] δ8 71 (t, J 5.5 Hz, 1H, NH), 8.65 (s, 1H, H-3), 7.40 (s, 1H, H-6), 3.56 (t, J=4.6 Hz, 4H, CH$_2$(CH$_2$)O), 3.24 (q, J=6.0 Hz, 2H, NHCH$_2$), 2.48 (s, 4H, aziridine-H), 2.34 (br s, 4H, N(CH$_2$)CH$_2$), 2.29 (t, J=6.8 Hz, 2H, CH$_2$Nmorph), 1.59–1.45, m, 4H, CH$_2$(CH$_2$)$_2$). Anal. Calcd for C$_{17}$H$_{23}$N$_5$O$_6$: C, 51.90;H, 5.89; N, 17.81. Found: 52.25;H, 5.78; N, 17.60%

Example F

Preparation of 5-(aziridin-1-yl)-N-[2-(imidazol-1-yl) ethyl]-2,4-dinitrobenzamide (7). Similar reaction of crude 5-chloro-2,4-dinitrobenzoyl chloride in $Et_2O$ with N[-2-(aminoethyl)]imidazole (2 equiv) in water, followed by direct recrystallization of the product from EtOAc, gave 5-chloro-N-[2-(imidazol-1-yl)ethyl]-2,4-dinitrobenzamide (49%): mp >300° C., $^1$H NMR [$(CD_3)_2SO$] δ9 04 (t, J=5.6 Hz, 1H, NH), 8.44 (s, 1H, H-3), 8.03 (s, 1H, H-6), 7.69, 7.24, 6.92 (3xs, 3H, imidazole-H), 4.15 (t, J=5 8 Hz, 2H, NHCH$_2$CH$_2$), 3.57 (q, J=5 8 Hz, 2H, NHCH$_2$). Anal. Calcd for $C_{12}H_{10}ClN_5O_6$: C, 42.43,H, 2.97, N, 20.62. Found: C, 42 52;H, 2.89, N, 20.06%.

A stirred suspension of the above benzamide (150 mg, 0.44 mmol) in THF (40 mL) was treated with aziridine (91 μL, 1.76 mmol) at room temperature for 4 h, then additional aziridine (91 μL) was added. After a further 4 h, the mixture was concentrated under reduced pressure below 25° C., and the residue was partitioned between EtOAc and saturated NaCl. Evaporation of the organic layer gave a product that was triturated with EtOAc then recrystallized from MeCN/EtOAc/petroleum ether to give 7 (56 mg, 37%): mp >250° C.; $^1$H NMR [$(CD_3)_2SO$] δ8.91 (t, J=5.6 Hz, 1H, NH), 8.66 (s, 1H, H-3), 7.67 (s, 1H, imidazole-H), 7.29 (s, 1H, H-6), 7.24 & 6.93 (2xs, 2H, imidazole-H), 4 16 (t, J=5.9 Hz, 2H, NHCH$_2$CH$_2$), 3 62–3.51 (m, 2H, NHCH$_2$), 2.49 (s, 4H, aziridine-H). Anal. Calcd. for $C_{14}H_{14}N_6O_5$: C, 48.55;H, 4.07; N, 24.27. Found: C, 48.69;H, 4.00; N, 24.10%.

Example G

Preparation of 5-(aziridin-1-yl)-N-[2-(methoxycarbonyl)ethyl]-2,4-dinitrobenzamide (8). A solution of 5-chloro-2,4-dinitrobenzoic acid (10.0 g, 40 mmol) in SOCl$_2$ (100 mL) containing DMF (2 drops) was heated under reflux for 5 h, and then concentrated to dryness and azeotroped with benzene. A solution of the resulting crude acid chloride in $Et_2O$ was added to a vigorously-stirred suspension of methyl 3-aminopropanoate hydrochloride (6.22 g, 44 mmol) and Et3N (13.9 mL, 100 mmol) in $Et_2O$ (100 mL). after stirrign for 30 min, the resulting precipitate was filtered off, washed well with water, and recrystallized from EtOAc/petroleum ether to give 5-chloro-N-[2-(methoxycarbonyl)ethyl]-2,4-dinitrobenzamide (6.24 g, 47%), mp 139–141° C. $^1$H NMR [$(CD_3)_2SO$] δ8.98 (t, J=5.6 Hz, 1H, CONH), 8.83 (s, 1H, H-3), 8.09 (s, 1H, H-6), 3.63 (s, 3H, OCH$_3$), 3.47 (dt, J=6.7, 5.6 Hz, 2H, CONCH$_2$), 2.61 (t, J=6.7 Hz, 2H, CH$_2$CO$_2$CH$_3$) Anal. Calcd for $C_{11}H_{10}ClN_3O_7$. C, 39.84;H, 3.04; N, 12.67, Cl, 10 69. Found: C, 40.07;H, 2.79; N, 12 55; Cl, 10.92%.

A stirred solution of the above amide (315 mg, 0.95 mmol) in $CH_2Cl_2$ (35 mL) was treated with aziridine (197 μL, 3.81 mmol) at room temperature for 8 h. The mixture was partitioned between more $CH_2Cl_2$ and water, and the organic layer was dried and concentrated under reduced pressure. The residue was dissolved in EtOAc and filtered through a short column of silica gel to give 8 (269 mg, 84%): mp ($CH_2Cl_2$/iPr$_2$O) 137° C.; $^1$H NMR [$(CD_3)_2SO$] δ8.86 (t, J=5.6 Hz, 1 H, NH), 8.66 (s, 1H, H-3), 7.40 (s, 1H, H-6), 3.63 (s, 3H, Me), 3.51–3.43 (m, 2H, NHCH$_2$), 2.61 (t, J=6 8 Hz, 2H, CH$_2$CO), 2 48 (s, 4H, aziridine-H). Anal. Calcd for $C_{13}H_{14}N_4O_7$: C, 46.15;H, 4 17; N, 16 57. Found: C, 45.89,H, 3.89; N, 16.45%.

Example H

Preparation of 3-(aziridin-1-yl)-4-nitrobenzamide (9) 3-Fluoro-4-nitrobenzoic acid (Schmelkes and Rubin, J. Amer. Chem. Soc. 1944, 66, 1631–1632) was converted to the acid chloride (SOCl$_2$/DMF), and then reacted with conc. NH$_4$OH in $Et_2O$ to give 3-fluoro-4-nitrobenzamide (92%): mp (EtOAc/petroleum ether) 165–166° C., $^1$H NMR [(CD$_3$)$_2$SO] δ8.31 (br s, 1H, NHH), 8.26 (t, J=8.1 Hz, 1H, H-5), 7.98 (dd, J=12.1, 1.7 Hz, 1H, H-2), 7.89 (dd, J=8.6, 1.1 Hz, 1H, H-6), 7.86 (br s, 1 , NHH). Anal. Calcd for $C_7H_5FN_2O_3$. C, 45.66;H, 2.74; N, 15.21. Found: C, 45 63;H, 2.54, N, 15.22%.

A stirred solution of the above benzamide (100 mg, 0.54 mmol) in dry MeCN (4 mL) was treated with aziridine (168 μL, 3.24 mmol) at room temperature for 4 h. The resulting precipitate was collected, washed with cold water, and crystallized twice from EtOAc to give 9 (46 mg, 41%). mp 223–224° C.,; $^1$H NMR [$(CD_3)_2SO$] δ8.21 (br s, 1H, NHH), 7 99 (d, J=8.5 Hz, 1H, H-5), 7.69 (d, J=1.8 Hz, 1H, H-2), 7.67 (br s, 1H, NHH), 7.56 (dd, J=8 5, 1.8 Hz, 1H, H-6), 2.30 (s, 4H, (CH$_2$)$_2$). Anal. Calcd for $C_9H_9N_3O_3$: C, 52.17;H, 4.38, N, 20.28. Found C, 52 10;H, 4.30, N, 20.07%.

Example I

Preparation of 5-(aziridin-1-yl)-N-(2,3-dihydroxypropyl)-2-(methylsulfonyl)-4-nitrobenzamide (10) A mixture of 5-chloro-2-(methylsulfonyl)-4-nitrobenzoic acid (Somani et al., Br. J. Cancer 1994, 69 (Suppl. XXI), 38) (2.21 g, 7.9 mmol) and SOCl$_2$ (20 mL) containing DMF (2 drops) was refluxed for 1 h, then evaporated to dryness under reduced pressure. The resulting crude acid chloride was dissolved in anhydrous $Me_2CO$ (40 mL), and the solution was cooled to −5° C. and treated in one portion with a cold solution of 3-aminopropane-1,2-diol (1.48 g, 1.62 mmol) in water (20 mL). The mixture was shaken at room temperature for 15 min, then diluted with water (20 mL) and concentrated under reduced pressure to ca. 30 mL. After addition of solid NaCl, the mixture was extracted with EtOAc (3x), and the extracts were worked up to give a solid. This was dissolbed in EtOAc and filtered through a column of silica gel to give 5-chloro-N-(2,3-dihydroxypropyl)-2-(methylsulfonyl)-4-nitrobenzamide (2.54 g, 91%), mp (EtOAc/iPr$_2$O) 141–142° C. $^1$NMR [$(CD_3)_2SO$] δ8.83 (t, J=5.7 Hz, 1H, NH), 8.55 (s, 1 , H-3), 8.08 (s, 1H, H-6), 4.81 (d, J=5.0 Hz, 1H, CHOH), 4.55 (t, J=5.8 Hz, 1H, CH$_2$OH), 3.70–3.58 (m, 1H, CHOH), 3.45 (s, 3H, CH$_3$), 3.44–3.35 (m, 3H, CH$_2$OH & CONHCHH), 3.17–3.06 (m, 1H, CONHCHH). Anal. Calcd for $C_{11}H_{13}ClN_2O_7S$: C, 3 71; N, 7.94; S, 9.09 Found: C, 37.73;H, 3.96; N, 7.83; S, 9.29%.

A solution of the above benzamide (0.84 g, 2.38 mmol) and aziridine (0 74 mL, 14 3 mmol) in EtOAc (20 mL) was stirred at room temperature for 16 h. The reaction mixture was worked up and the residue was chromatographed on silica gel, eluting with EtOAc/MeOH (4:1) to give 10 (0.65 g, 76%), mp (EtOAc) 120–123° C. $^1$H NMR [$(CD_3)_2SO$] δ8.71 (t, J=5.8 Hz, 1H, NH), 8.45 (s, 1H, H-3), 744 (s, 1H, H-6), 477 (d, J=5 0 Hz, 1H, CHOH), 4.54 (t, J=5 8 Hz, 1H, CH$_2$OH), 3.70–361 (m, 1H, CHOH), 3.45–3.36 (m, 3H, CH$_2$OH, CONHCHH), 3 41 (s, 3H, CH$_3$), 3.17–3.07 (m, 1H, CONHCHH), 2.47 (s, 4H, aziridine-H). Anal. Calcd for $C_{13}H_{17}N_3O_7S.0.5H_2O$: C, 42.39,H, 4.93; N, 11.41. Found C, 41.98; H, 5.11, N, 10.97%.

Example J

Preparation of 5-(aziridin-1-yl)-2-nitrobenzamide (11). A stirred solution of 2-nitro-5-fluorobenzamide (Orrin, Eur. Pat. Appl. 19,388; Chem. Abstr. 1981, 94, 156538h) (480 mg, 2.61 mmol) in dry DMSO (2 mL) was treated with aziridine (0.54 mL, 10.4 mmol) at room temperature under N$_2$ for 48 h, then poured into cold water (50 mL). Prolonged cooling at −5° C. gave a crystalline product that was collected and filtered throuhg a column of silica gel in EtOAc to give 11 (256 mg, 47%), mp (EtOAc) 172–174° C. $^1$H NMR [$(CD_3)_2SO$] δ8.01 & 7.61 (2xs, 2H, CONH2), 7.93 (d, J=8.9 Hz, 1H, H-3), 7.17 (dd, J=8.8, 2.4 Hz, 1H, H-4), 7.09 (d, J=2.3 Hz, 1H-6), 2.24 (s, 4H, aziridine-H ). Anal. Calcd. for $C_9H_9N_3O_3$: 52.17;H, 4.38; N, 20.29 Found: C, 52.29;H, 4.27; N, 20.25%.

Example K

Preparation of 5-(aziridin-1-yl)-4-(methylsulfonyl)-2-nitrobenzamide (12). A stirred suspension of 5-fluoro-4-

(methysulfonyl)-2-nitrobenzamide (Atwell et al., Anti-Cancer Drug Design, 1996, 11, 553–567) (262 mg, 1.00 mmol) in dry dioxane (15 mL) was treated with aziridine (207 μL, 4.00 mmol) at 35° C. for 1 h. The solvent was then removed under reduced pressure, and the residue was shaken with water and recrystallized from MeOH to give 12 (217 mg, 76%) mp 222–224° C., $^1$H NMR [(CD$_3$)$_2$SO]δ8.39 (s, 1H, H-3), 8.14 & 7 86 (2xbr s, 2H, CONH$_2$), 7.33 (s, 1H, H-6), 3 41 (s, 3H, CH$_3$), 2.57 (s, 4H, aziridine-H). Anal. Calcd for C$_{10}$H$_{11}$N$_3$O$_5$S: C, 42.10,H, 3.89, N, 14.73. Found. C, 45.25;H, 3.71; N, 14 98%.

Example L

Preparation of 3-(aziridin-1-yl)-2,6-dinitrobenzamide (13). A solution of 3-chloro-2,6-dinitrobenzamide (Palmer et al., J. Med. Chem., 1996, 29, 2518–2528) (0.50 g, 2.04 mmol) and aziridine (1.00 g, 0.023 mol) in EtOAc (80 mL) was stirred at room temperature for 18 h. After washing with water the solution was dried over Na$_2$SO$_4$ and concentrated under reduced pressure to ca. 20 mL. Petroleum ether was added until a slight cloudiness persisted and the solution was chilled at −20° C. to give 13: mp 206–210° C. (dec.); $^1$H NM [(CD$_3$)$_2$SO] δ8.26 (br s, 1H, CONH), 8.24 (d, J=9.0 Hz, 1H, H-5), 7.92 (br s, 1H, CONH), 7.44 (d, J=9.0 Hz, 1H, H-4), 2.35 (s, 4H, aziridine-H); $^{13}$C NMR δ162.67 (s), 150.63 (s), 141.82 (s), 139.32 (s), 128.17 (s), 127.77 (d), 123.31 (d), 28.41 (t). Anal. Calcd for C$_9$H$_8$N$_4$O$_5$; C, 42.86;H, 3.20; N, 22.22. Found: C, 42.97;H, 3.15; N, 22.32%.

Example M

Preparation of 2-(aziridin-1-yl)-3,5-dinitrobenzamide(14) Reaction of 2-chloro-3,5-dinitrobenzamide [Palmer et al., J.Med.Chem. 1996, 39, 2518–2528] in ethyl acetate as described in Example C except that the reaction time was 2 hours, gave 2-aziridin-1-yl)-3,5-dinitrobenzamide (14) as a yellow powder, mp 200° C. [Kahn & Ross, Chem-Biol. Int., 1969–70,1, 27–47, record mp 196° C.]$^1$H NMR [CD$_3$)$_2$SO] δ8 74 (d, J=2.6 Hz, 1H, H-4), 8.35(d,J=2 Hz, 1H, H-6), 8.10, 7 93 (2 br s,2H, CONH$_2$), 2.40 (s, 4H, aziridine-H) $^{13}$NMR δ

Example N

Preparation of 2-(Aziridin-1-yl)-4 chloro-5-nitrobenzamide(15). Reaction of 4-chloro-2,5-dinitrobenzamide [Goldstein and Schaaf, Helv. Chim Acta. 1957, 40, 369–376] in tetrahydrofuran as described in Example C except that the reaction time was 2 hours, gave 2-(aziridin-1-yl)-4-chloro-5-nitrobenzamide (15) as a yellow powder, mp 155° C. $^1$H NMR [(CD$_3$)$_2$SO] δ8.15 (s, 1H, H-6), 7.83, 7 81 (2 br s, 2H, CONH$_2$), 7.40 (s, 1H, H-3),2.33 (s, 4H, aziridin-H). $^{13}$NMR δ165.68 (s), 156 66 (s), 140.39 (s), 128 46 (s), 127 87 (s), 127 02 (d), 123.94 (d), 29.35 (t). Found: C,44.70;H, 3.14; N, 17.41. C$_9$H$_8$ClN$_3$O$_3$ requires C, 44 73;H, 3.33; N, 17.39%

Example O

Preparation of 2-(aziridin-1-yl)-4-chloro-3-nitrobenzamide (16).

Reaction of 4-chloro-2,3-dinitrobenzamide [Goldstein and Schaaf, Helv. Chim. Acta. 1957, 40, 369–376] in ethyl acetate generally as described in Example L, except that the reaction time was 3 hours, gave 2-(aziridin-1-yl)-4-chloro-3-nitrobenzamide (16) as a yellow powder, mp 216° C. $^1$H NMR [(CD$_3$)$_2$SO] δ8 16 (br s, 1H CONHH), 7 71 (br s, 1H, CONHH), 7 69 (d, J=8.3 Hz, 1H, H-6), 7.25 (d, J=8.3 Hz, 1H, H-5), 2.28 (s, 4H, aziridine-H) $^{13}$C NMR δ165.53 (s), 142.59 (s), 142.49 (s), 131 65 (d), 129.71 (s), 129.00 (s), 121.37 (d), 29.40 (t). Found. C, 44.90;H, 3.49; N, 17.39. C$_9$H$_8$ClN$_3$O$_3$ requires C, 44.73;H, 3.33; N, 17.39%.

Example P

Preparation of 2-(aziridin-1-yl)-N-(2,3-dihydroxypropyl)-3,5-dinitrobenzamide (17). A stirred solution of 2-chloro-N-(2,3-dihydroxypropyl)-3,5-dinitrobenzamide (Palmer et al., J. Med. Chem. 1996, 39, 2518–2528) (670 mg, 2.10 mmol) in EtOAc (35 mL) was treated with aziridine (325 μL, 6 28 mmol) at room temperature for 3 h, then concentrated under reduced pressure. The residue was dissolved in warm EtOAc (220 mL) and filtered though a short column of silica gel to give 17 (304 mg, 44%). mp (EtOAc/petroleum ether) 154–155° C., $^1$NMR [(CD$_3$)$_2$SO] δ8.74 (d, J=2.7 Hz, 1H, H-4), 8.57 (t, J=5 6 Hz, 1H, NH), 8.36 (d, J=2.7 Hz, 1 H, H-6), 4 88 (d, J=5.3 Hz, 1H, CHOH), 4.64 (t, J=5.7 Hz, 1H, CH$_2$OH), 3 73–3 63 (m, 1H, CHOH), 3.52–3.42 (m, 1H, NHCHH), 3.42–3.34 (m, 2H, CH$_2$OH), 3.26–3.15 (m, 1H, NHCHH), 2.39 (s, 4H, aziridine-H). Anal. Calcd for C$_{12}$H$_{14}$N$_4$O$_7$. C, 44.2;H, 4.3, N, 17.2. Found: C, 44.3;H, 4.2, N, 17.3%.

Example Q

Preparation of 2-(aziridin-1-yl)-N-[2-(4-morpholino) ethyl]-3,5-dinitrobenzamide (18). A solution of 2-chloro-3,5-dinitrobenzoyl chloride (2.58 g, 9.74 mmol) in dry Et$_2$O (30 mL) was cooled to 5° C. and treated in one portion with a solution of 4-(2-aminoethyl)morpholine (2.61 g, 20 mmol) in water (30 mL). After shaking the mixture vigorously at room temperature for 5 min, the resultant solid was collected and crystallized from EtOAc to give 2-chloro-N-[2-(4-morpholino)ethyl]-3,5-dinitrobenzamide (3.07 g, 88%). mp 188–190° C., $^1$NMR [(CD$_3$)$_2$SO] δ9.00 (d, J=2.6 Hz, 1H, H-4), 8.00 (t, J=5.3 Hz, 1H, NH), 8.51 (d, J=2.6 Hz, 1H, H-6), 3.58 (t, J=4.5 Hz, 4H, CH$_2$(CH$_2$)O, 3.45–3.36 (m, 2H, NHCH$_2$), 2.53–2 46 (m, partially obscured, 2H, NHCH$_2$CH$_2$), 2.42 (br s, 4H, N(CH$_2$)CH$_2$). Anal. Calcd for C$_{13}$H$_{15}$ClN$_4$O$_6$. C, 43.5;H, 4.2; N, 15.6%. Found: 43.8;H, 4.3, N, 15.5%.

A stirred solution of the above benzamide (660 mg, 1.84 mmol) in CH$_2$Cl$_2$ (60 mL) was treated with aziridine (286 μL, 5.52 mmol) at room temperature for 3 h The solution was then washed with water, dried and evaporated, and the residue as crystallized (2x) from CH$_2$Cl$_2$/iPr$_2$O to give 18 (548 mg, 82%). mp 176–177° C.; $^1$H NMR [(CD$_3$)$_2$SO] δ8.75 (d, J=2.7 Hz, 1H, H-4), 8.58 (t, J=5.5 Hz, 1H, NH), 8 34 (d, J=2.7 Hz, 1H, H-6), 3.58 (t, J=4 5 Hz, 4H, O(CH$_2$)$_2$), 3.43 (q, J=6.2 Hz, 2H, NHCH$_2$), 2.54–2 48 (m, partially obscured, 2H, NHCH$_2$CH$_2$), 2.46–2 36 (m, 8H, N(CH$_2$) CH$_2$, aziridine-H) Anal. Calcd for C$_{15}$H$_{19}$N$_5$O$_6$ 0.25H$_2$O: C, 48.71;H, 5.31; N, 18.94. Found. C, 49.31,H, 5.24; N, 19.17%

Example R 4-(Aziridin-1-yl)-3,5-dinitrobenzamide (19). Reaction of 4-chloro-3,5-dinitrobenzamide (Ullman et al., Annalen, 1909, 366, 82) with aziridine in EtOAc as above for 2 h gave 19: mp 228–231° C., $^1$H NMR [(CD$_3$)$_2$SO] δ8.68 (s, 2H, H-2,6), 8.33, 7.75 (2 br s, 2H, CONH$_2$), 2.36 (s, 4H, aziridine-H), $^{13}$NMR 163.77 (s), 145 16 (s), 143.40 (s), 128.43 (d), 125.89 (s), 30 61 (t). Anal. Calcd for C$_9$H$_8$N$_4$O$_5$: C, 42.86;H, 3.20, N, 22.22. Found: C, 43.15,H, 2.98; N, 22.13%.

Biological Activity

Selected compounds of Table 1, representative of formula (I), were evaluated for cytotoxicity (measured as IC$_{50}$ values in μM following an 18 h drug exposure) in three sets of mammalian cell lines, and the results are given in Table 2. The Chinese hamster fibroblast NR− line (T78-1) is a V79/4 Chinese hamster fibroblast transfected with an empty shuttle vector, while the NR+ line (T79-A3) is the corresponding NR transfectant. The human colon carcinoma NR− line (WIDR) is wild-type, while the NR+ line (WC14 10) is the corresponding NR transfectant. The human ovarian carcinoma NR− line (SKOV3) is wild-type, while the NR+ line (SC3.2) is the corresponding NR transfectant. EMT6 is a mouse mammary carcinoma line, and EN2A is the NR-transformed counterpart. Ratios of $IC_{50}s(NR+/NR−)$ provide the major measure of efficiency of activation (these sometimes do not strictly agree with the NR− and $NR+IC_{50}$ values because they are inter-experiment averages).

TABLE 2

Biological data for selected nitrophenylaziridines of Table 1.

| No | V-79 NR− | V-79 NR+ | V-79 ratio | WiDr NR− | WiDr NR+ | WiDr ratio | SKOV NR− | SKOV NR+ | SKOV ratio | EMT6 NR− | EMT6 NR+ | EMT6 ratio |
|---|---|---|---|---|---|---|---|---|---|---|---|---|
| 2 | 210 | 0.71 | 381 | 147 | 3.7 | 49 | 170 | 2.3 | 84 | 90 | 1.1 | 86 |
| 3 | 571 | 0.15 | 4160 | 131 | 0.72 | 183 | 494 | 0.45 | 1100 | 229 | 0.061 | 4505 |
| 4 | 364 | 1.8 | 235 | 170 | 8.1 | 21 | 533 | 13 | 46 | | | |
| 5 | 255 | 0.048 | 6210 | 30 | 0.23 | 120 | 122 | 0.15 | 730 | | | |
| 6 | 237 | 0.25 | 1210 | 28 | 0.31 | 93 | 151 | 0.30 | 510 | | | |
| 7 | 420 | 0.39 | 1170 | 47 | 1.0 | 48 | 61 | 0.58 | 104 | | | |
| 8 | 581 | 0.40 | 1580 | 124 | 2.3 | 51 | 677 | 2.5 | 270 | | | |
| 9 | 108 | 62 | 1.4 | 102 | 62 | 1.6 | 93 | 61 | 1.6 | | | |
| 10 | 641 | 8.8 | 87 | 826 | 26 | 33 | 920 | 6.2 | 159 | 454 | 3.7 | 124 |
| 11 | 121 | 81 | 1.5 | 126 | 89 | 1.4 | 129 | 102 | 1.4 | | | |
| 12 | 419 | 40 | 12 | 224 | 22 | 10 | 393 | 22 | 19 | | | |
| 13 | 437 | 135 | 3.8 | 312 | 58 | 5.9 | 584 | 66 | 9.5 | 287 | 27 | 10 |
| 17 | 1440 | 6 | 208 | 878 | 12 | 71 | 1300 | 7.3 | 184 | | | |
| 18 | >500 | 7.3 | >68 | 521 | 18 | 32 | >500 | 11 | >72 | | | |
| 19 | >20 | >20 | ND | >20 | >20 | ND | >20 | >20 | ND | >20 | >20 | ND |
| 14 | 1082 | 1.2 | 864 | 1080 | 13 | 85 | 1700 | 6.1 | 280 | 769 | 1.3 | 626 |
| CB1954 | 395 | 0.3 | 1200 | 56 | 1.2 | 51 | 182 | 0.58 | 357 | 90 | 0.08 | 1100 |

What is claimed is:

1. A compound of the formula (Ia):

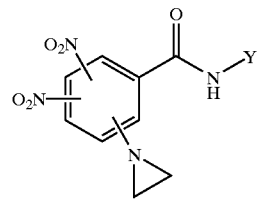

(Ia)

wherein Y is a lower alkyl group having 1 to 6 carbon atoms and being substituted with one or more of the following groups: methylcarboxy, imidazolyl and morpholinyl.

2. A compound according to claim 1, wherein the compound is 5-(aziridin-1-yl)-N-[2-(4-morpholino)ethyl]-2,4-dinitrobenzamide.

3. A compound according to claim 1, wherein the compound is 5-(aziridin-1-yl)-N-[3-(4-morpholino)propyl]-2,4-dinitrobenzamide.

4. A compound according to claim 1, wherein the compound is N-[4-(4-morpholino)butyl]-5-(aziridin-1-yl)-2,4-dinitrobenzamide.

5. A compound according to claim 1, wherein the compound is 5-(aziridin-1-yl)-N-[2-(imidazol-1-yl)ethyl]-2,4-dinitrobenzamide.

6. A compound according to claim 1, wherein the compound is 5-(aziridin-1-yl)-N-[2-(methoxycarbonyl)ethyl]-2,4-dinitrobenzamide.

7. A two component system for the treatment of neoplastic disease which comprises:

(i) a vector encoding and capable of expressing a nitroreductase enzyme in a tumour cell, or a tumour-directed antibody linked to a nitroreductase enzyme; and (ii) a compound of formula (Ia):

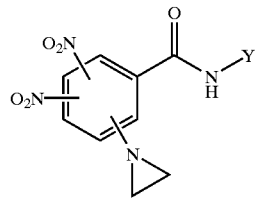

(Ia)

wherein Y is a lower alkyl group having 1 to 6 carbon atoms and being substituted with one or more of the following groups: methylcarboxy, imidazolyl and morpholinyl.

8. A method of treating neoplastic disease which comprises administering to a patient in need of such treatment a therapeutically effective amount of a two component system which comprises:

(i) a vector encoding and capable of expressing a nitroreductase enzyme in a tumour cell, or a tumour-directed antibody linked to a nitroreductase enzyme; and (ii) a compound of formula (Ia):
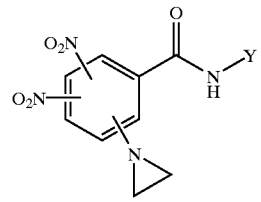
(Ia)
wherein Y is a lower alkyl group having 1 to 6 carbon atoms and being substituted with one or more of the following groups: methylcarboxy, imidazolyl and morpholinyl.
* * * * *